United States Patent
Wang et al.

(10) Patent No.: US 8,648,222 B2
(45) Date of Patent: *Feb. 11, 2014

(54) METHOD FOR MAKING CATALYST COMPOSITIONS OF ALKALI METAL HALIDE-DOPED BIVALENT METAL FLUORIDES AND A PROCESS FOR MAKING FLUORINATED OLEFINS

(75) Inventors: Haiyou Wang, Amherst, NY (US); Hsueh Sung Tung, Getzville, NY (US)

(73) Assignee: Honeywell International Inc., Morristown, NJ (US)

(*) Notice: Subject to any disclaimer, the term of this patent is extended or adjusted under 35 U.S.C. 154(b) by 222 days.

This patent is subject to a terminal disclaimer.

(21) Appl. No.: 13/176,856

(22) Filed: Jul. 6, 2011

(65) Prior Publication Data

US 2011/0282111 A1 Nov. 17, 2011

Related U.S. Application Data

(60) Division of application No. 12/275,656, filed on Nov. 21, 2008, now Pat. No. 8,119,557, and a continuation-in-part of application No. 12/167,159, filed on Jul. 2, 2008.

(60) Provisional application No. 61/012,566, filed on Dec. 10, 2007, provisional application No. 60/958,468, filed on Jul. 6, 2007.

(51) Int. Cl.
*C07C 17/00* (2006.01)

(52) U.S. Cl.
USPC .............................. 570/158; 570/155; 570/157

(58) Field of Classification Search
USPC .......................................... 570/158, 155, 157
See application file for complete search history.

(56) References Cited

U.S. PATENT DOCUMENTS

| | | | |
|---|---|---|---|
| 1,681,751 A | 8/1928 | Henry | |
| 3,591,646 A | 7/1971 | Vecchio et al. | |
| 4,111,991 A | 9/1978 | Garrison | |
| 4,113,655 A | 9/1978 | Pieters et al. | |
| 4,194,990 A | 3/1980 | Carlson et al. | |
| 4,465,786 A | 8/1984 | Zimmer et al. | |
| 5,276,240 A | 1/1994 | Timmons et al. | |
| 6,524,990 B2 | 2/2003 | Syvret et al. | |
| 7,592,287 B2 | 9/2009 | Kemnitz et al. | |
| 2005/0090698 A1 | 4/2005 | Merkel et al. | |
| 2007/0112230 A1 | 5/2007 | Mukhopadhyay et al. | |
| 2007/0129579 A1 | 6/2007 | Wang et al. | |
| 2007/0197842 A1 | 8/2007 | Mukhopadhyay et al. | |
| 2009/0030247 A1 | 1/2009 | Johnson et al. | |
| 2009/0299107 A1 | 12/2009 | Wang et al. | |

FOREIGN PATENT DOCUMENTS

RU 2277068 5/2006

*Primary Examiner* — Jafar Parsa
(74) *Attorney, Agent, or Firm* — Bruce O. Bradford

(57) ABSTRACT

There is provided methods for making a catalyst composition represented by the formula $MX/M'F_2$ wherein MX is an alkali metal halide; M is an alkali metal ion selected from the group consisting of $Li^+$, $Na^+$, $K^+$, $Rb^+$, and $Cs^+$; X is a halogen ion selected from the group consisting of $F^-$, $Cl^-$, $Br^-$, and $I^-$; $M'F_2$ is a bivalent metal fluoride; and M' is a bivalent metal ion. There is also a method for making a fluorinated olefin.

8 Claims, No Drawings

METHOD FOR MAKING CATALYST COMPOSITIONS OF ALKALI METAL HALIDE-DOPED BIVALENT METAL FLUORIDES AND A PROCESS FOR MAKING FLUORINATED OLEFINS

CROSS-REFERENCE TO RELATED APPLICATIONS

This application is a Divisional of U.S. application Ser. No. 12/275,656, filed on Nov. 21, 2008 (now U.S. Pat. No. 8,119, 557), which claims priority benefit of U.S. Provisional Application No. 61/012,566, filed on Dec. 10, 2007, each of which are incorporated herein by reference.

This application is also a Continuation-In-Part of U.S. application Ser. No. 12/167,159, filed on Jul. 2, 2008 (now pending), which claims priority benefit of U.S. Provisional Application No. 60/958,468, filed on Jul. 6, 2007, each of which are incorporated herein by reference.

BACKGROUND OF THE INVENTION

1. Field of the Invention

The present invention relates to a method for making catalyst compositions of alkali metal halide-doped bivalent metal fluorides. The present invention also relates to a process for making fluorinated olefins with the catalyst compositions.

2. Description of the Related Art 2,3,3,3-tetrafluoropropene (1234yf), a hydrofluoroolefin that exhibits low global warming potential, can be used in a variety of applications, for example, as a refrigerant, a blowing agent, a solvent, a cleaning agent, and a monomer for macromolecular compounds.

One process for making 1234yf entails the dehydrochlorination of 1,1,1,2-tetrafluoror-2-chloropropane (244bb). U.S. Provisional Application 60/958,468, filed Jul. 6, 2007, discloses a process for making 1234yf by dehydrochlorinating 244bb in the presence of catalysts of bivalent metal fluorides doped with alkali metal halides.

There is a need for commercially viable methods for preparing catalysts of bivalent metal fluorides doped with alkali metal halides.

SUMMARY OF THE INVENTION

According to the present invention, there is provided a method for making a catalyst composition. The catalyst composition is represented by the formula $MX/M'F_2$. MX is an alkali metal halide. M is an alkali metal ion selected from the group consisting of $Li^+$, $Na^+$, $K^+$, $Rb^+$, and $Cs^+$. X is a halogen ion selected from the group consisting of $F^-$, $Cl^-$, $Br^-$, and $I^-$. $M'F_2$ is a bivalent metal fluoride. M' is a bivalent metal ion. The method has the following steps: (a) dissolving an amount of the alkali metal halide in an amount of solvent sufficient to substantially dissolve or solubilize the alkali metal halide to form an alkali metal halide solution; (b) adding an amount of the bi-valent metal fluoride to the alkali metal halide solution to form a slurry of the alkali metal halide and bi-valent metal fluoride; and (c) removing substantially all of the solvent from the slurry to form a solid mass of the alkali metal halide and bi-valent metal fluoride.

According to the present invention, there is provided a method for making a catalyst composition. The method has the following steps: (a) an amount of hydroxide, oxide, or carbonate of an alkali metal is added to an aqueous solution of a hydrogen halide and reacted to form an aqueous solution of an alkali metal halide; (b) an amount of a hydroxide, oxide, or carbonate of a bivalent metal is added to an aqueous solution of hydrogen fluoride and reacted to form a precipitate of a bivalent metal fluoride therein; (c) admixing the alkali metal halide solution and the precipitate of the bivalent metal fluoride to form an aqueous slurry; and (d) removing water from the aqueous slurry to form a solid mass.

Still further according to the present invention, there is provided process for making a fluorinated olefin. The process has the step of dehydrochlorinating a hydrochlorofluorocarbon having at least one hydrogen and at least one chlorine on adjacent carbons in the presence of a catalytically effective amount of a catalyst composition represented by the formula $MX/M'F_2$. MX is an alkali metal halide. M is an alkali metal ion selected from the group consisting of $Li^+$, $Na^+$, $K^+$, $Rb^+$, and $Cs^+$. X is a halogen ion selected from the group consisting of $F^-$, $Cl^-$, $Br^-$, and $I^-$. $M'F_2$ is a bivalent metal fluoride. M' is a bivalent metal ion.

DETAILED DESCRIPTION OF THE INVENTION

Catalyst compositions that are useful products of the methods of the present invention are combinations/admixtures of an alkali metal halide(s) and a bivalent metal fluoride(s) that can be represented by the following:

$$MX/M'F_2$$

wherein MX is an alkali metal halide; M is an alkali metal ion selected from the group consisting of $Li^+$, $Na^+$, $K^+$, $Rb^+$, and $Cs^+$. X is a halogen ion selected from the group consisting of F, $Cl^-$, $Br^-$, and $I^-$. X is preferably $F^-$ and $Cl^-$. $M'F_2$ is a bivalent metal fluoride. M' is a bivalent metal ion. M' is preferably selected from the group consisting of $Mg^{2+}$, $Ca^{2+}$, $Sr^{2+}$, $Ba^{2+}$, $Ni^{2+}$, $Fe^{2+}$, $Co^{2+}$, $Cu^{2+}$, and $Zn^{2+}$. M' is most preferably $Mg^{2+}$.

The catalyst compositions can alternately be represented by the following:

$$n\% \ MX/M'F_2$$

wherein n % is the weight percentage of alkali metal halide in the composition based upon the total weight of the composition. The alkali metal halide is preferably from about 0.05 wt % to about 50 wt %, more preferably about 5 wt % to about 15 wt %, and most preferably about 7.5 wt % to about 12.5 wt % of the catalyst composition based on the total weight of the catalyst composition.

Examples of alkali metal halides include LiCl, NaCl, KCl, RbCl, CsCl, LiF, NaF, KF, RbF, and CsF. Preferred alkali metal halides include KCl, CsCl, KF, and CsF. Examples of bi-valent metal fluorides include $MgF_2$, $CaF_2$, $SrF_2$, $BaF_2$, $NiF_2$, $FeF_2$, $CoF_2$, $CuF_2$, and $ZnF_2$. Preferred bi-valent metal fluorides include $MgF_2$ and $NiF_2$.

The alkali metal halide is added to an amount of solvent sufficient to substantially dissolve or solubilize the alkali metal halide. The preferred solvent is one in which the alkali metal halide is readily soluble. The choice of solvent may vary depending on the particular alkali metal halide(s). Examples of solvents that can be used for the preparation of the catalyst compositions of the present invention include water, alcohols, ethers, and mixtures thereof. Useful alcohols include monohydric and polyhydric alcohols. Most preferred alcohols are those that are monohydric and have 1 to 5 carbon atoms. A most preferred solvent is water.

In one embodiment of the method of the invention, the bi-valent metal fluoride is added to the solution of the alkali metal halide to form a slurry. After formation of the slurry, substantially all of the solvent is removed to form a solid mass of a mixture of the alkali metal halide and bi-valent metal fluoride. Although the solvent can be removed in one step, a preferred method is to drive off a portion of the solvent from the slurry to form a paste and then follow by drying the paste to form the solid mass. Any conventional technique can be used to drive off the solvent. Examples of such techniques include vigorous stirring at room or elevated temperatures, evaporation, settling and decanting, centrifugation, and filtration. It is preferred to evaporate off a desired amount of solvent to form the paste. The paste is then dried by any suitable method to form a free-flowing, substantially solvent-free powder. Preferred methods for drying include oven drying, most preferably at temperatures from about 110° C. to about 120° C., and spray drying. Being solvent free means that less than 1 wt. %, preferably about 0.5 wt % or less, more preferably about 0.1 wt % or less, and most preferably no solvent will remain with the powder after solvent removal/drying. Upon removal of solvent, the powder will take the form of a solid mass (or powder) of a mixture of particles of the alkali metal halide and the bi-valent metal fluoride.

In another embodiment of the method of the present invention, a slurry of the alkali metal halide and the bivalent metal fluoride is prepared by a different, reactive technique. In a first step, a hydroxide, oxide, or carbonate of an alkali metal is added to an aqueous solution of a hydrogen halide and reacted to form an aqueous solution of an alkali metal halide. In a second step, a hydroxide, oxide, or carbonate of a bivalent metal is added to an aqueous solution of hydrogen fluoride and reacted to form a precipitate of a bivalent metal fluoride therein. In a third step, the alkali metal halide solution and the bivalent metal fluoride precipitate are then admixed to form an aqueous slurry. In a fourth step, water is then removed from the aqueous slurry in the manner described herein to form a solid mass.

Optionally, the solid mass of the mixture of the alkali metal halide and the bi-valent metal fluoride powder is then calcined. Calcination is preferably carried out at a temperature of about 100° C. to about 750° C., more preferably at a temperature of about 200° C. to about 600° C., and most preferably at a temperature of about 300° C. to about 600° C. Calcination may further optionally be carried out in the presence of an inert gas, such as nitrogen or argon.

After calcination, the powder is optionally further grinded such that it becomes more finely-divided. The powder is further optionally pelletized in order to form pellets. The pellets then provide catalyst surfaces to use in actual process application.

The catalyst compositions of the present invention may afford performance advantages over compositions that are obtained by simple dry mixing of components. A more complete degree of intermixing may be achieved. The complete degree of mixing may manifest itself in higher selectivity to the target product, such as 1234yf (and less to the formation of a dehydrofluorinating product, such as 1233xf).

The catalyst compositions are useful in converting hydrochlorofluorocarbons to fluorinated olefins. Useful hydrochlorofluorocarbons have at least one hydrogen and at least one chlorine on adjacent carbons.

Table 1 sets forth examples of fluorinated olefins and precursor hydrochlorofluorocarbons from which they can be obtained (precursor hydrochlorofluorocarbon in left column and corresponding product fluorinated olefin in the right column).

TABLE 1

| Hydrochlorofluorocarbon | Fluorinated Olefin(s) |
|---|---|
| chlorotetrafluoropropane | tetrafluoropropene |
| chloropentafluoropropane | pentafluoropropene |
| chlorohexafluoropropane | hexafluoropropene |
| 1,1,1,2-tetrafluoro-2-chloropropane $CF_3CFClCH_3$ (244bb) | 2,3,3,3-tetrafluoropropene $CF_3CF=CH_2$ (1234yf) |
| 1,1,1,2-tetrafluoro-3-chloropropane $CF_3CHFCH_2Cl$ (244eb) | 2,3,3,3-tetrafluoropropene $CF_3CF=CH_2$ (1234yf) |
| 1,1,1,3-tetrafluoro-3-chloropropane $CF_3CH_2CHFCl$ (244fa) | 1,3,3,3-tetrafluoropropene $CF_3CH=CHF$ (trans/cis-1234ze) |
| 1,1,1,3-tetrafluoro-2-chloropropane $CF_3CHClCH_2F$ (244db) | 1,3,3,3-tetrafluoropropene $CF_3CH=CHF$ (trans/cis-1234ze) |
| 1,1,1,2,3-pentafluoro-2-chloropropane $CF_3CFClCH_2F$ (235bb) | 1,2,3,3,3-pentafluoropropene $CF_3CF=CHF$ (Z/E-1225ye) |
| 1,1,1,2,3-pentafluoro-3-chloropropane $CF_3CHFCHFCl$ (235ea) | 1,2,3,3,3-pentafluoropropene $CF_3CF=CHF$ (Z/E-1225ye) |
| 1,1,1,3,3-pentafluoro-3-chloropropane $CF_3CH_2CF_2Cl$ (235fa) | 1,1,3,3,3-pentafluoropropene $CF_3CH=CF_2$ (1225zc) |
| 1,1,1,3,3-pentafluoro-2-chloropropane $CF_3CHClCHF_2$ (235da) | 1,1,3,3,3-pentafluoropropene $CF_3CH=CF_2$ (1225zc) |
| 1,1,1,2,3,3-hexafluoro-2-chloropropane $CF_3CFClCHF_2$ (226ba) | 1,1,2,3,3,3-hexafluoropropene $CF_3CF=CF_2$ (1216) |
| 1,1,1,2,3,3-hexafluoro-3-chloropropane $CF_3CHFCF_2Cl$ (226ea) | 1,1,2,3,3,3-hexafluoropropene $CF_3CF=CF_2$ (1216) |

The following are examples of the invention and are not to be construed as limiting.

EXAMPLES

In the following examples, 244bb is dehydrochlorinated to 1234yf in the presence of the catalysts of combinations of alkali metal halides and bivalent metal fluorides.

Example 1

244bb Dehydrohalogenation Over $CsCl/MgF_2$ Catalysts Having Various CsCl Loadings A series of $CsCl/MgF_2$ catalysts with various loadings of CsCl were tested to determine the effect of CsCl loading on reactivity. 20 cc of catalyst pellets was typically used. A mixture of 97.2%/2.0% 244bb/1233xf was passed through catalyst bed at a rate of 6 g/h (grams/hour) at a temperature ranging from 470° C. to 520° C. The temperatures at the bottom and top of the catalyst bed were measured. As shown in Table 2 below, activity remained at about the same level regardless of loading, while the selectivity to 1233xf (a non-desired dehydrofluorination product) decreased as CsCl loading increased to 5.0 wt %. No 1233xf was formed over the 10 wt % $CsCl/MgF_2$ catalyst.

TABLE 2

(Effect of CsCl loading on the performance of $CsCl/MgF_2$ catalysts during 244bb dehydrohalogenation*)

| CsCl loading (wt %) | Temp. Bottom-Top (°) | time (h) | Conversion, (%) 244bb | Selectivity (%) 1234yf | Selectivity (%) 1233xf | Selectivity (%) others |
|---|---|---|---|---|---|---|
| 0.0 | 475-506 | 1 | 48.2 | 76.9 | 17.7 | 5.4 |
|  | 475-509 | 2 | 52.9 | 79.8 | 14.6 | 5.6 |
|  | 475-509 | 3 | 53.3 | 80.7 | 12.9 | 6.4 |
|  | 475-507 | 4 | 52.4 | 81.4 | 11.9 | 6.7 |
|  | 475-509 | 5 | 54.2 | 83.0 | 10.9 | 6.1 |
|  | 475-510 | 6 | 54.1 | 83.6 | 10.2 | 6.2 |
|  | 475-508 | 7 | 54.7 | 84.7 | 9.6 | 5.7 |

TABLE 2-continued (Effect of CsCl loading on the performance of CsCl/MgF$_2$ catalysts during 244bb dehydrohalogenation*)

| CsCl loading (wt %) | Temp. Bottom-Top (°) | time (h) | Conversion, (%) 244bb | Selectivity (%) 1234yf | Selectivity (%) 1233xf | Selectivity (%) others |
|---|---|---|---|---|---|---|
| | 475-509 | 8 | 53.7 | 85.4 | 9.2 | 5.4 |
| | 475-510 | 9 | 54.9 | 86.0 | 8.6 | 5.5 |
| | 475-509 | 10 | 53.5 | 86.7 | 8.2 | 5.1 |
| 2.5 | 500-514 | 1 | 48.4 | 88.7 | 5.2 | 6.1 |
| | 500-514 | 2 | 48.1 | 88.5 | 5.2 | 6.3 |
| | 500-514 | 3 | 49.5 | 89.1 | 5.0 | 5.9 |
| | 500-507 | 4 | 46.9 | 89.3 | 4.8 | 5.9 |
| | 500-509 | 5 | 48.5 | 89.9 | 4.6 | 5.5 |
| | 500-513 | 6 | 48.5 | 89.6 | 4.7 | 5.7 |
| | 500-514 | 7 | 49.6 | 89.9 | 4.6 | 5.5 |
| 5.0 | 490-510 | 1 | 49.0 | 94.8 | 0.5 | 4.7 |
| | 490-511 | 2 | 51.0 | 94.5 | 0.4 | 5.1 |
| | 490-510 | 3 | 49.2 | 95.3 | 0.5 | 4.2 |
| | 490-505 | 4 | 48.7 | 95.0 | 0.4 | 4.6 |
| | 490-507 | 6 | 49.8 | 95.4 | 0.4 | 4.2 |
| | 490-503 | 8 | 49.2 | 95.7 | 0.4 | 3.9 |
| 10.0 | 475-511 | 1 | 49.6 | 96.9 | | 3.1 |
| | 475-510 | 2 | 51.2 | 97.0 | | 3.0 |
| | 475-511 | 3 | 51.8 | 96.9 | | 3.1 |
| | 475-508 | 4 | 50.4 | 96.9 | | 3.1 |
| | 475-510 | 5 | 51.4 | 97.0 | | 3.0 |

*Reaction conditions: 20 ml of catalyst, 6 grams organic/hour, 97.2% 244bb/2.0% 1233xf, 1 atm pressure Example 2

244bb Dehydrohalogenation Over 10 wt % Alkali Metal Chloride/MgF$_2$ Catalysts 10 wt % KCl/MgF$_2$ and 10 wt % CsCl/MgF$_2$ catalysts were tested. 20 cc of catalyst pellets was used. A mixture of 99.1%/0.4% 244bb/1233xf was passed through the catalyst bed at a rate of 6 g/h at a temperature ranging from 380° C. to 480° C. The temperature at the bottom and top of the catalyst bed were measured. As shown in Table 2, both catalysts exhibited about the same activity (20%), while the 10 wt % CsCl/MgF$_2$ catalyst provided a higher selectivity to 1234yf without generation of 1233xf over the catalyst.

TABLE 3

(Reactivity of 10 wt % KCl/MgF$_2$ and 10 wt % CsCl/MgF$_2$ Catalysts during 244bb Dehydrohalogenation*)

| Catalyst | Temp. Bottom-Top (°) | time (hour) | Conversion (%) 244bb | Selectivity (%) 1234yf | Selectivity (%) 1233xf | Selectivity (%) others |
|---|---|---|---|---|---|---|
| 10 wt % KCl/MgF$_2$ | 405-477 | 1 | 21.9 | 89.1 | 0.4 | 10.5 |
| | 405-480 | 2 | 17.8 | 95.2 | 0.6 | 4.2 |
| | 405-480 | 4 | 20.0 | 95.8 | 0.6 | 3.6 |
| | 405-480 | 6 | 21.2 | 96.0 | 0.6 | 3.7 |
| | 405-480 | 8 | 20.1 | 96.1 | 0.6 | 3.3 |
| | 405-480 | 10 | 21.5 | 96.2 | 0.6 | 3.1 |
| | 405-480 | 12 | 20.9 | 96.2 | 0.6 | 3.2 |
| | 405-479 | 14 | 20.5 | 96.3 | 0.6 | 3.1 |
| | 405-479 | 16 | 20.2 | 96.2 | 0.6 | 3.2 |
| | 405-479 | 18 | 20.1 | 96.3 | 0.6 | 3.1 |
| | 405-480 | 20 | 20.5 | 96.4 | 0.6 | 3.0 |
| | 405-478 | 22 | 20.4 | 96.4 | 0.6 | 3.0 |
| | 405-478 | 24 | 19.9 | 96.3 | 0.6 | 3.1 |
| 10 wt % CsCl/MgF$_2$ | 380-481 | 1 | 10.3 | 91.1 | 0.0 | 8.9 |
| | 380-481 | 2 | 14.0 | 95.9 | 0.0 | 4.1 |
| | 380-482 | 4 | 16.8 | 96.7 | 0.0 | 3.3 |
| | 380-484 | 6 | 19.6 | 97.4 | 0.0 | 2.6 |

TABLE 3-continued (Reactivity of 10 wt % KCl/MgF$_2$ and 10 wt % CsCl/MgF$_2$ Catalysts during 244bb Dehydrohalogenation*)

| Catalyst | Temp. Bottom-Top (°) | time (hour) | Conversion (%) 244bb | Selectivity (%) 1234yf | Selectivity (%) 1233xf | Selectivity (%) others |
|---|---|---|---|---|---|---|
| | 380-482 | 8 | 20.0 | 97.5 | 0.0 | 2.5 |
| | 380-481 | 10 | 20.5 | 97.5 | 0.0 | 2.5 |
| | 380-481 | 12 | 20.6 | 97.8 | 0.0 | 2.2 |
| | 380-479 | 14 | 19.9 | 97.7 | 0.0 | 2.3 |
| | 380-478 | 16 | 20.0 | 97.8 | 0.0 | 2.2 |
| | 380-481 | 18 | 21.0 | 97.8 | 0.0 | 2.2 |
| | 380-483 | 20 | 21.8 | 98.0 | 0.0 | 2.0 |
| | 380-481 | 22 | 20.7 | 97.7 | 0.0 | 2.3 |
| | 380-481 | 24 | 19.7 | 97.6 | 0.0 | 2.4 |

*Reaction conditions: 20 ml of catalyst, 6 grams organic/hour, 99.1%/0.4% 244bb/1233xf, 1 atm pressure Example 3

244bb Dehydrohalogenation Over 10 wt % CsCl/Bi-Valent Metal Fluoride Catalysts 10 wt % CsCl/NiF$_2$ and 10 wt % CsCl/MgF$_2$ catalysts were tested. 20 cc of catalyst pellets was used. A mixture of 99.1%/0.4% 244bb/1233xf was passed through a catalyst bed at a rate of 6 g/h at a temperature ranging from 380° C. to 480° C. The temperature at the bottom and top of the catalyst bed were measured. As shown in Table 4, both catalysts exhibited about the same selectivity to 1234yf (97% to 98%), while the 10 wt % CsCl/MgF$_2$ catalyst provided higher activity.

TABLE 4

(Reactivity of MgF$_2$ and Alkaline Metal Chloride-Doped MgF$_2$ Catalysts during 244bb Dehydrohalogenation*)

| Catalyst | Temp. Bottom-Top (°) | time (hour) | Conversion (%) 244bb | Selectivity (%) 1234yf | Selectivity (%) 1233xf | Selectivity (%) others |
|---|---|---|---|---|---|---|
| 10 wt % CsCl/NiF$_2$ | 410-482 | 1 | 5.6 | 86.3 | 0.0 | 13.7 |
| | 410-482 | 2 | 8.3 | 90.4 | 0.0 | 9.6 |
| | 410-483 | 4 | 9.9 | 93.6 | 0.0 | 6.4 |
| | 410-480 | 6 | 10.1 | 95.2 | 0.0 | 4.8 |
| | 410-481 | 8 | 10.9 | 95.9 | 0.0 | 4.1 |
| | 410-480 | 10 | 12.0 | 96.2 | 0.0 | 3.8 |
| | 410-481 | 12 | 13.2 | 96.8 | 0.0 | 3.2 |
| | 410-482 | 14 | 14.2 | 97.1 | 0.0 | 2.9 |
| | 410-481 | 16 | 14.4 | 97.3 | 0.0 | 2.7 |
| | 410-481 | 18 | 14.7 | 97.3 | 0.0 | 2.7 |
| | 410-480 | 20 | 14.8 | 97.4 | 0.0 | 2.6 |
| | 410-481 | 22 | 15.1 | 97.8 | 0.0 | 2.2 |
| | 410-480 | 24 | 15.4 | 97.6 | 0.0 | 2.4 |
| 10 wt % CsCl/MgF$_2$ | 380-481 | 1 | 10.3 | 91.1 | 0.0 | 8.9 |
| | 380-481 | 2 | 14.0 | 95.9 | 0.0 | 4.1 |
| | 380-482 | 4 | 16.8 | 96.7 | 0.0 | 3.3 |
| | 380-484 | 6 | 19.6 | 97.4 | 0.0 | 2.6 |
| | 380-482 | 8 | 20.0 | 97.5 | 0.0 | 2.5 |
| | 380-481 | 10 | 20.5 | 97.5 | 0.0 | 2.5 |
| | 380-481 | 12 | 20.6 | 97.8 | 0.0 | 2.2 |
| | 380-479 | 14 | 19.9 | 97.7 | 0.0 | 2.3 |
| | 380-478 | 16 | 20.0 | 97.8 | 0.0 | 2.2 |
| | 380-481 | 18 | 21.0 | 97.8 | 0.0 | 2.2 |
| | 380-483 | 20 | 21.8 | 98.0 | 0.0 | 2.0 |
| | 380-481 | 22 | 20.7 | 97.7 | 0.0 | 2.3 |
| | 380-481 | 24 | 19.7 | 97.6 | 0.0 | 2.4 |

*Reaction conditions: 20 ml of catalyst, 6 grams organic/hour, 99.1% 244bb/0.4% 1233xf, 1 atm pressure

Example 4

244bb Dehydrohalogenation Over Alkaline Metal Chloride-Doped MgF$_2$ Catalysts In Example 4, a series of alkaline metal chlorides were investigated as an additive to MgF$_2$ with a purpose of improving the selectivity to 1234yf. For comparison purpose, the results obtained over MgF$_2$ catalyst were also reported. 20 cc of catalyst pellets was used in a typical run. A mixture of 97.2% 244bb/2.0% 1233xf was passed through catalyst bed at a rate of 6 g/h (grams/hour) at a temperature ranged from 470° C. to 520° C. The temperatures at the bottom of catalyst bed and at the top of catalyst bed were measured.

As shown in Table 5, the MgF$_2$ provided a 244bb conversion of 53-55%, a 1234yf selectivity of 80-87%, and a 1233xf selectivity of 8-15%; the 10% LiCl/MgF$_2$ provided a 244bb conversion below 45%, a 1234yf selectivity of about 90%, and a 1233xf selectivity of about 5%; the 10% KCl/MgF$_2$ provided a 244bb conversion below 50%, a 1234yf selectivity of about 96%, and a 1233xf selectivity of about 1%; and the 10% CsCl/MgF$_2$ provided a 244bb conversion of 50-52%, a 1234yf selectivity of about 97%, and no formation of 1233xf. CsCl exhibited the best results. The 10% CsCl/MgF$_2$ catalyst provided activity comparable to MgF$_2$ and the highest 1234yf selectivity while generating no 1233xf.

TABLE 5

(Reactivity of alkaline metal chloride-doped MgF$_2$ catalysts during 244bb dehydrohalogenation*)

| Catalyst | Temp. Bottom-Top (°) | t (h) | Conversion 244bb (%) | Selectivity 1234yf (%) | Selectivity 1233xf (%) | Selectivity, Unknowns (%) |
|---|---|---|---|---|---|---|
| 10 wt % LiCl/MgF$_2$ | 475-490 | 1 | 29.4 | 89.1 | 5.3 | 5.6 |
| | 475-506 | 2 | 38.8 | 89.6 | 5.3 | 5.0 |
| | 475-505 | 3 | 40.4 | 89.9 | 5.2 | 4.9 |
| | 475-507 | 4 | 42.9 | 90.5 | 4.8 | 4.7 |
| 10 wt % KCl/MgF$_2$ | 475-514 | 1 | 38.3 | 95.1 | 0.9 | 4.0 |
| | 475-515 | 3 | 47.2 | 95.6 | 0.8 | 3.6 |
| | 475-515 | 5 | 47.5 | 95.8 | 0.7 | 3.5 |
| | 475-509 | 6 | 43.7 | 95.8 | 0.6 | 3.5 |
| | 475-514 | 7 | 47.1 | 95.8 | 0.7 | 3.5 |
| 10 wt % CsCl/MgF$_2$ | 475-511 | 1 | 49.6 | 96.9 | | 3.1 |
| | 475-510 | 2 | 51.2 | 97.0 | | 3.0 |
| | 475-511 | 3 | 51.8 | 96.9 | | 3.1 |
| | 475-508 | 4 | 50.4 | 96.9 | | 3.1 |
| | 475-510 | 5 | 51.4 | 97.0 | | 3.0 |

*Reaction conditions: 20 ml of catalyst, 6 grams-organic/hour, 97.2% 244bb/2.0% 1233xf, pressure = 1 atm Additional teachings to catalyst compositions having mixtures/combinations of alkali metal halides and bivalent metal fluorides and use of same in dehydrochlorinating hydrofluorocarbons to fluorinated olefins is shown in U.S. Provisional Patent Application No. 60/958,468, filed Jul. 6, 2007, which is incorporated herein by reference.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making a fluorinated olefin, comprising: dehydrochlorinating a hydrochlorofluorocarbon having at least one hydrogen and at least one chlorine on adjacent carbons in the presence of a catalytically effective amount of a catalyst composition represented by the following:

MX/M'F$_2$ wherein MX is an alkali metal halide; M is an alkali metal ion selected from the group consisting of Li$^+$, Na$^+$, K$^+$, Rb$^+$, and Cs$^+$; X is a halogen ion selected from the group consisting of F$^-$, Cl$^-$, Br$^-$, and I$^-$; M'F$_2$ is a bivalent metal fluoride; and M' is a bivalent metal ion.

2. The process of claim 1, wherein the hydrochlorofluorocarbon and the fluorinated olefin are each selected from the groups consisting of the following:

| Hydrochlorofluorocarbon | Fluorinated olefin |
|---|---|
| chlorotetrafluoropropane | tetrafluoropropene |
| chloropentafluoropropane | pentafluoropropene |
| chlorohexafluoropropane | hexafluoropropene |
| 1,1,1,2-tetrafluoro-2-chloropropane CF$_3$CFClCH$_3$ (244bb) | 2,3,3,3-tetrafluoropropene CF$_3$CF=CH$_2$ (1234yf) |
| 1,1,1,2-tetrafluoro-3-chloropropane CF$_3$CHFCH$_2$Cl (244eb) | 2,3,3,3-tetrafluoropropene CF$_3$CF=CH$_2$ (1234yf) |
| 1,1,1,3-tetrafluoro-3-chloropropane CF$_3$CH$_2$CHFCl (244fa) | 1,3,3,3-tetrafluoropropene CF$_3$CH=CHF (trans/cis-1234ze) |
| 1,1,1,3-tetrafluoro-2-chloropropane CF$_3$CHClCH$_2$F (244db) | 1,3,3,3-tetrafluoropropene CF$_3$CH=CHF (trans/cis-1234ze) |
| 1,1,1,2,3-pentafluoro-2-chloropropane CF$_3$CFClCH$_2$F (235bb) | 1,2,3,3,3-pentafluoropropene CF$_3$CF=CHF (Z/E-1225ye) |
| 1,1,1,2,3-pentafluoro-3-chloropropane CF$_3$CHFCHFCl (235ea) | 1,2,3,3,3-pentafluoropropene CF$_3$CF=CHF (Z/E-1225ye) |
| 1,1,1,3,3-pentafluoro-3-chloropropane CF$_3$CH$_2$CF$_2$Cl (235fa) | 1,1,3,3,3-pentafluoropropene CF$_3$CH=CF$_2$ (1225zc) |
| 1,1,1,3,3-pentafluoro-2-chloropropane CF$_3$CHClCHF$_2$ (235da) | 1,1,3,3,3-pentafluoropropene CF$_3$CH=CF$_2$ (1225zc) |
| 1,1,1,2,3,3-hexafluoro-2-chloropropane CF$_3$CFClCHF$_2$ (226ba) | 1,1,2,3,3,3-hexafluoropropene CF$_3$CF=CF$_2$ (1216) |
| 1,1,1,2,3,3-hexafluoro-3-chloropropane CF$_3$CHFCF$_2$Cl (226ea) | 1,1,2,3,3,3-hexafluoropropene CF$_3$CF=CF$_2$ (1216). |

3. The method of claim 1, wherein M' is selected from the group consisting of Mg$^{2+}$, Ca$^{2+}$, Sr$^+$, Ba$^{2+}$, Ni$^{2+}$, Fe$^{2+}$, Co$^{2+}$, Cu$^{2+}$, and Zn$^{2+}$.

4. The method of claim 1, wherein the alkali metal halide is from about 0.05 wt % to about 50 wt % of the catalyst composition based on the total weight of the catalyst composition.

5. The method of claim 4, wherein the alkali metal halide is from about 5 wt % to about 15 wt % of the catalyst composition based on the total weight of the catalyst composition.

6. The method of claim 5, wherein the alkali metal halide is from about 7.5 wt % to about 12.5 wt % of the catalyst composition based on the total weight of the catalyst composition.

7. The method of claim 1, wherein M is selected from the group consisting of potassium and cesium, wherein X is selected from the group consisting of F$^-$ and Cl$^-$, and wherein M' is selected from the group consisting of Mg$^{2+}$ and Ni$^{2+}$.

8. The method of claim 7, wherein M is cesium, X is Cl$^-$ or F$^-$ and M' is Mg$^{2+}$.

\* \* \* \* \*